(12) United States Patent
Staton et al.

(10) Patent No.: US 10,563,795 B2
(45) Date of Patent: Feb. 18, 2020

(54) FLEXIBLE POSEABLE SENSORS AND SENSOR MOUNT SYSTEMS AND METHODS

(71) Applicant: NEWTONOID TECHNOLOGIES, L.L.C., Liberty, MO (US)

(72) Inventors: Fielding B. Staton, Liberty, MO (US); David Strumpf, Columbia, MO (US)

(73) Assignee: Newtonoid Technologies, L.L.C., Liberty, MO (US)

( * ) Notice: Subject to any disclaimer, the term of this patent is extended or adjusted under 35 U.S.C. 154(b) by 0 days.

(21) Appl. No.: 15/677,833

(22) Filed: Aug. 15, 2017

(65) Prior Publication Data
US 2019/0056047 A1 Feb. 21, 2019

(51) Int. Cl.
| | |
|---|---|
| G01B 5/00 | (2006.01) |
| F16L 11/08 | (2006.01) |
| B65D 63/10 | (2006.01) |
| F16L 11/02 | (2006.01) |
| F16G 11/08 | (2006.01) |
| F16L 3/137 | (2006.01) |
| F16M 11/40 | (2006.01) |
| F16M 13/04 | (2006.01) |
| A61B 5/00 | (2006.01) |

(52) U.S. Cl.
CPC ............ *F16L 11/081* (2013.01); *B65D 63/10* (2013.01); *F16G 11/08* (2013.01); *F16L 3/137* (2013.01); *F16L 11/02* (2013.01); *F16M 11/40* (2013.01); *F16M 13/04* (2013.01); *G01B 5/0002* (2013.01); *A61B 5/6831* (2013.01)

(58) Field of Classification Search
CPC .......... F16L 11/081; F16L 3/137; F16L 11/02; F16G 11/08; B65D 63/10; A61B 5/6831; G01B 5/0002
See application file for complete search history.

(56) References Cited

U.S. PATENT DOCUMENTS

| | | | | |
|---|---|---|---|---|
| 4,959,547 | A * | 9/1990 | Carroll | G01T 1/161 250/336.1 |
| 6,295,394 | B1 * | 9/2001 | Arab-Sadeghabadi | G01D 5/35306 250/227.14 |
| 6,848,663 | B2 * | 2/2005 | Olive | A01G 9/128 248/317 |
| 7,437,027 | B2 * | 10/2008 | Zerwekh | E21B 47/06 385/12 |
| 2005/0054905 | A1 * | 3/2005 | Corl | A61B 5/14539 600/309 |

(Continued)

OTHER PUBLICATIONS

PCT Application No. PCT/US18/46665, International Search Report and Written Opinion, dated Sep. 14, 2018, 12 pages.

*Primary Examiner* — Xin Y Zhong
(74) *Attorney, Agent, or Firm* — Lathrop GPM LLP

(57) ABSTRACT

Flexible sensor systems and sensor mounting devices and methods are disclosed. A sensor-mounting device includes an elongate tubular body made of foam so as to be flexibly manipulatable. The body has a bore extending between front and rear ends in a longitudinal direction. A sensor is located within the bore of the tubular body. Situated within the bore of the body is an inner tube having a central bore. The sensor is protected by and located within the central bore of the inner tube. The inner tube is more rigid than the body and allows the sensor system to be poseable and fixable into many non-permanent positions.

19 Claims, 7 Drawing Sheets

(56) References Cited

U.S. PATENT DOCUMENTS

| | | | |
|---|---|---|---|
| 2010/0089436 A1* | 4/2010 | Watters | H01L 31/0232 |
| | | | 136/246 |
| 2010/0278213 A1* | 11/2010 | Bernier | H01C 3/20 |
| | | | 374/185 |
| 2013/0172691 A1* | 7/2013 | Tran | A61B 8/488 |
| | | | 600/301 |

* cited by examiner

FLEXIBLE POSEABLE SENSORS AND SENSOR MOUNT SYSTEMS AND METHODS

BACKGROUND

The present disclosure relates to flexible sensor systems and sensor mount devices and methods. Some of the flexible sensor systems are modular and allow for connectivity with other sensor systems to be added to a main unit to increase functionality.

Sensors of all types are commonly used in homes, on users, and commercial buildings. A non-exhaustive list includes: smoke detectors, motion detectors, cameras, liquid detectors, heart monitors, humidity detectors, barometric pressure sensors, carbon monoxide detectors, and temperature sensors.

These sensors may be prefabricated to a specific size and mount having a particular shape and design for a specific singular use. They are configured for installation or wear in a specific singular location and are thus limited in application. Additionally, the sensors referred to above cannot be adjusted in length. There exists a need for a flexible poseable sensor system and method that is not permanently mounted.

SUMMARY

The following presents a simplified summary of the invention in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere.

In one embodiment, a sensor-mounting device includes an elongated tubular body with a front end, a rear end, and a bore extending between the front and rear ends in a longitudinal direction; and a sensor located within the bore of the tubular body. The tubular body is flexibly poseable and fixable into a non-permanent position.

BRIEF DESCRIPTION OF THE DRAWINGS

The drawings constitute a part of this specification and may include exemplary embodiments of the present disclosure and illustrate various objects and features thereof, wherein.

DETAILED DESCRIPTION

Figure 1:
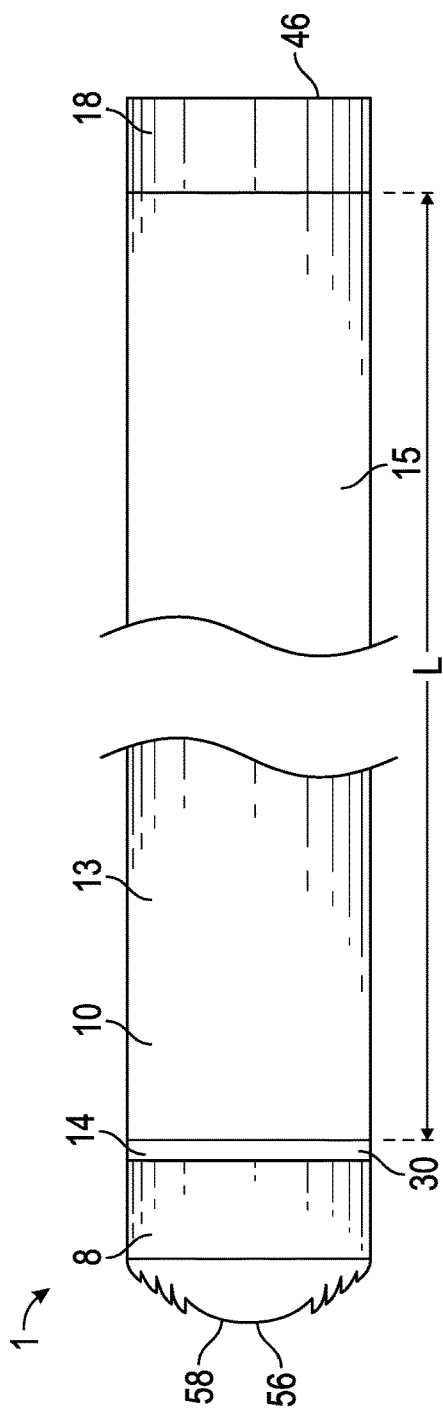
FIG. 1 is a side view of a sensor mounting system of FIG. 1.
Figure 2:
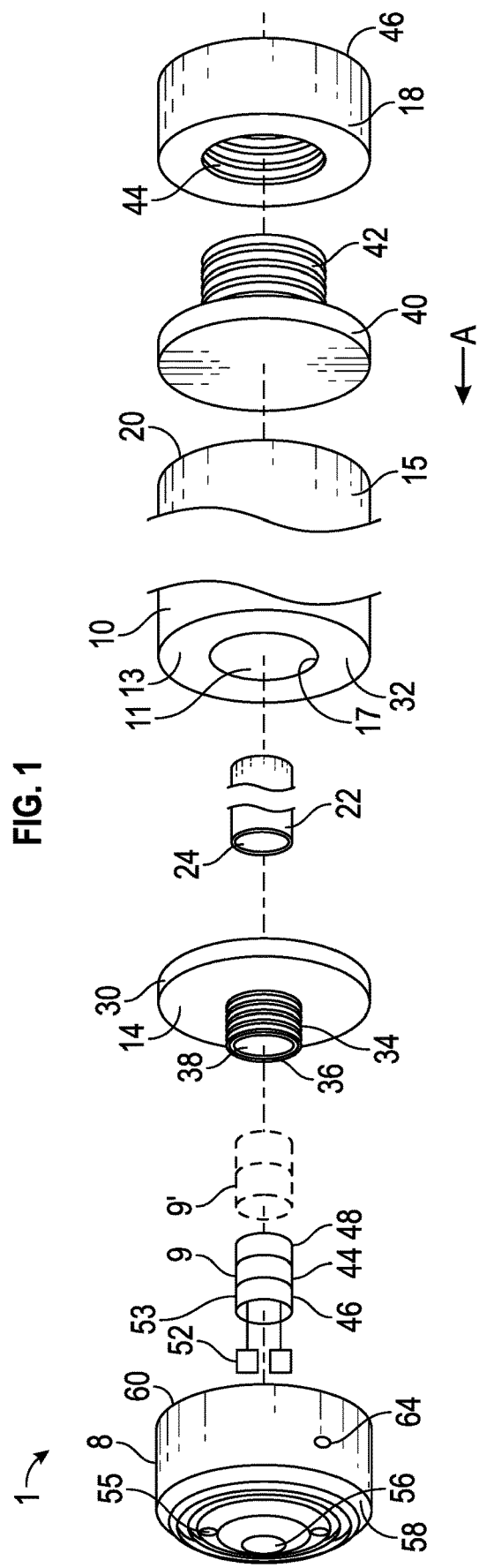
FIG. 2 is an exploded view of the sensor mounting system of FIG. 1.

Described herein are embodiments of extended remote access sensor and sensor mounting systems and methods designed to provide and/or make use of optical power, optical bidirectional data, auditory information, electrical power, electrical bidirectional data, etc. Sensors may communicate with mobile or wireless devices. As will be further understood from the description provided herein, the sensor and sensor-mounting systems and methods allow for increased flexibility in installation and ability to sense and provide controlled responses in areas that might not otherwise have been thought to be ideal for such purposes (e.g., around corners; around human necks, waists, wrists, ankles; around bike framing; around poles; etc.) The system allows for real-word interfacing in real-time based on human and/or environmental stimulus. Sensors are removably affixed in a desired location, and may be in communication with automated migrating remote accessories (e.g., telescopic poles, windows, doors, motorized tracks, drones, et cetera). The distributed functionality of the sensors and sensor-mounting systems and methods allow analysis of measureable information that can be derived through means of discrete sensor components.

FIGS. 1-4 illustrate a sensor-mounting system 1 adapted to be removably mounted. The sensor-mounting system 1 includes a sensor head 8, a sensor 9, and an elongated body 10. The sensor-mounting system 1 is illustrated as tubular shaped in a longitudinal direction A with a circular body 10. Nevertheless, the body 10 may be other geometrical shapes, such as square, rectangular, oval, et cetera. The body 10 may further include optical transmitters such as a light pipe or fiber optic materials, as is discussed in greater detail below. Further, the interior 17 may be layered with an electrical protective coating or layer of plastic.

Figure 3:
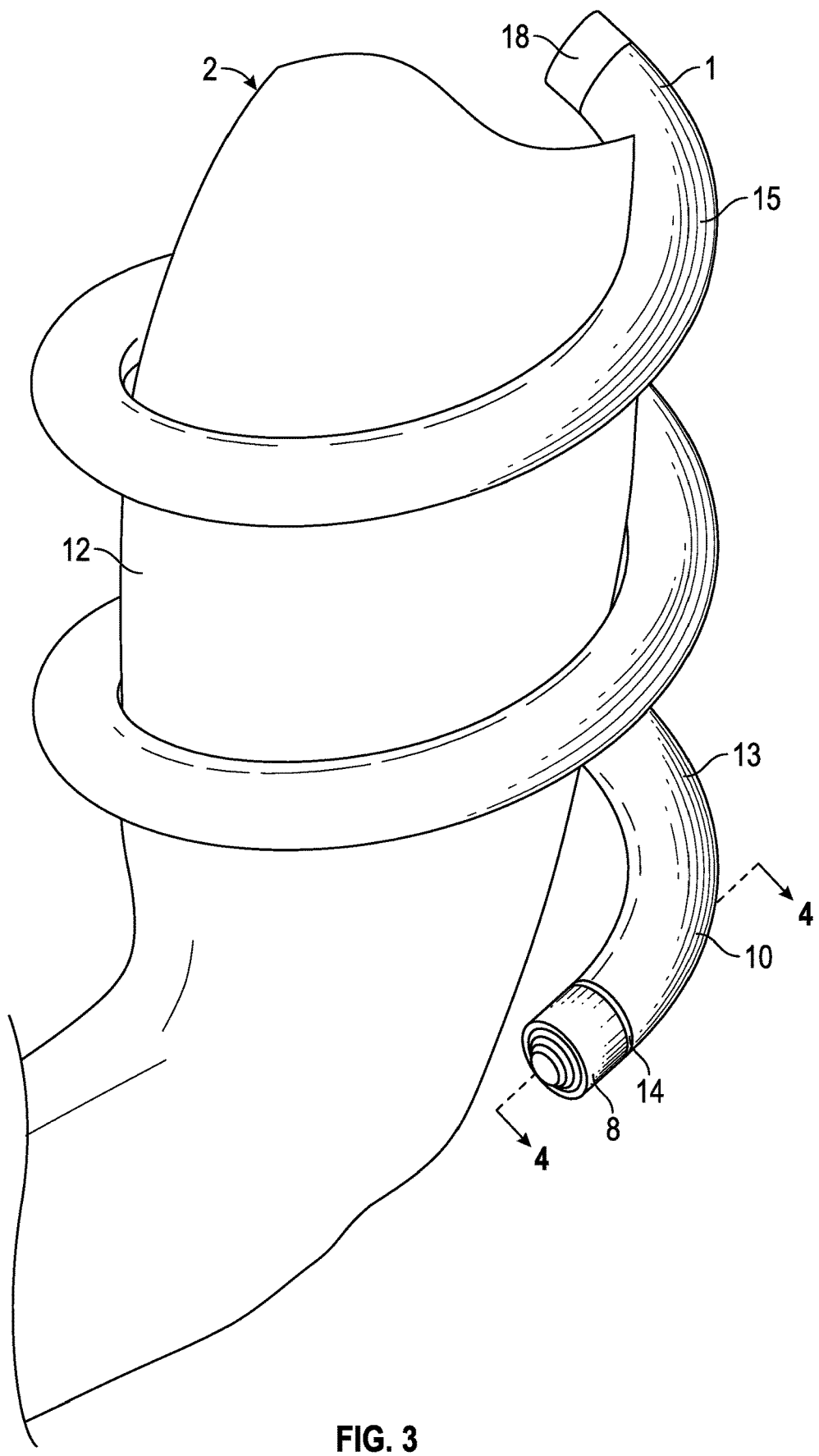
FIG. 3 is a perspective view of a sensor mounting system in use according to an embodiment of the present disclosure.

The body 10 has a central bore 11 defining an inner surface 17 in the longitudinal direction A. The exterior 15 of the body 10 may be constructed of a flexible, elastic material 13. The body 10 may be constructed of one or more materials 13 including but not limited to foam, quantum foam, polyurethane foam (foam rubber), extruded polystyrene (XPS) foam, polystyrene, phenolic, polycarbonate, or other such materials known or yet to be known. The material 13 allows a length L of the body 10 to be spun, looped, helixed, tied, crossed over, or otherwise manipulated and held in a non-permanent state until manipulated to another position or state. For example, FIG. 1 depicts the sensor mounting system 1 in an elongated non-permanent state; FIG. 3 depicts the sensor mounting system 1 in a helically wound non-permanent state around a bicep 12 of a user 2.

Figure 4:
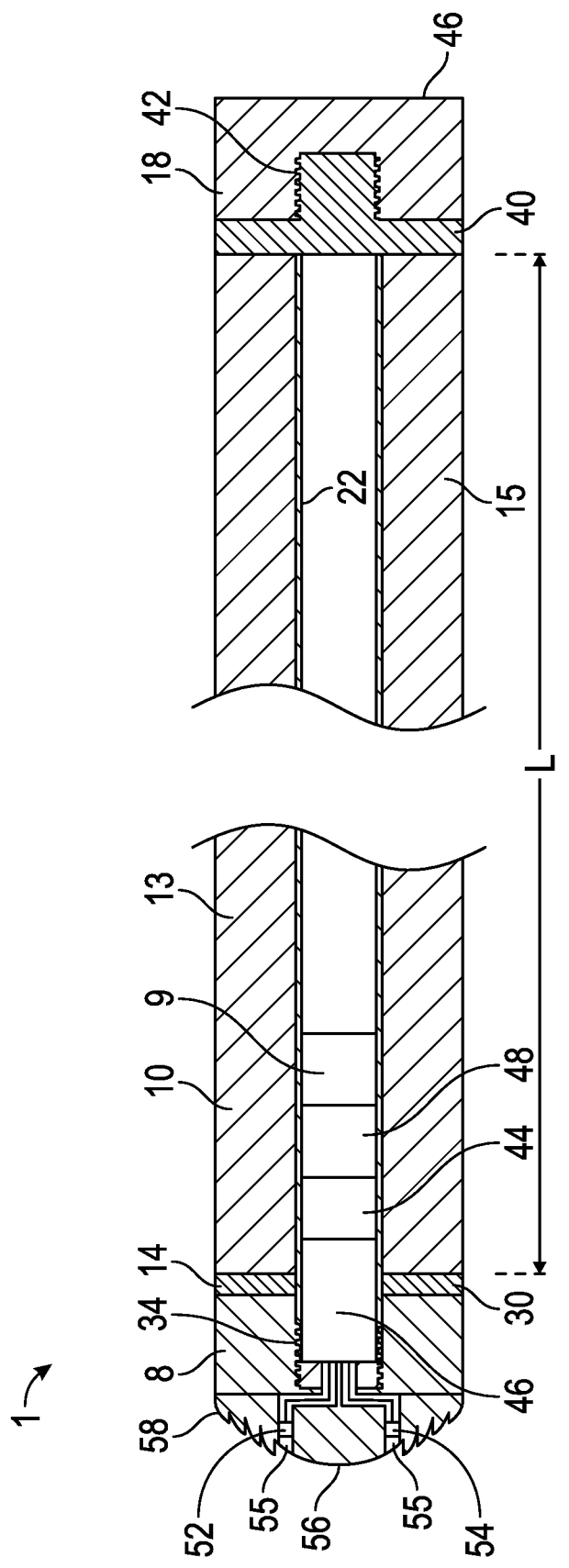
FIG. 4 is a cross-sectional view of the sensor mounting system of FIG. 1 taken along line 4-4.

The body 10 includes an inner tube 22 that is sized and shaped to be situated within the central bore 11 and surrounded by the material 13 (FIG. 4). The material 13 may have a memory to it, but an inner tube 22 maintains the body 10 in the non-permanent state. The inner tube 22 has a central bore 24 for which the sensor 9 and its components are situated within as will be further discussed below. The inner tube 22 is a housing that may accommodate sensor electronics and protects the electronic components from environmental influences. The inner tube 22 may have a length substantially similar to length L. The inner tube 22 may be constructed of a harder material and acts as a backbone to the body 10 to maintain a temporary state once the sensor mounting system 1 is positioned. However, those of skill in the art shall recognize that it may be desirable for the inner tube 22 to additionally be constructed of a durable, flexible, poseable material, the material being more rigid than the body 10. The inner tube 22 may be made from one or more materials including but not limited to plastic (e.g., bakelite, polystyrene, polycarbonate, polyvinyl, nylon, et cetera), or other appropriate materials known or yet to be known.

The body 10 includes a coupling 14, such as a liquid-tight coupling 14 on a first end 16 and an end cap 18 on a second end 20 to seal off the second end 20 of the body 10. The coupling 14 may have a radial circular plate or flange 30 on a first end 32 and a threaded portion 34 extending outwardly from the circular plate 30 to form the second end 36 of the coupling 14. The coupling 14 may have a central bore 38, which may be substantially similar in radius to the central bore 24 of the inner tube 22, as the inner tube 22 is configured to pass through the central bore 24 of the coupling 14. The plate 30 may have a radius substantially similar to that of the body 10. It is foreseen that the plate 30 may be larger in radius than the body 10. Likewise, the central bore 38 may be different in radius from the central bore 24 of the inner tube 22.

The end cap 18 may be a cylindrical protective cover that covers a second coupling or coupling means 40 at the second end 20 of the body 10. The second coupling 40 has a threaded projection 42 that is sized and shaped to mate with a threaded aperture 44 in the end cap 18. The second coupling 40 is sized and shaped as such that a second sensor mounting system 100 may be coupled to the sensor mounting system 1 as is further discussed below. In one embodiment, the end cap 18 may have an outer surface with a tip at a first end 46 for being driven into a material or the ground.

Figure 5:
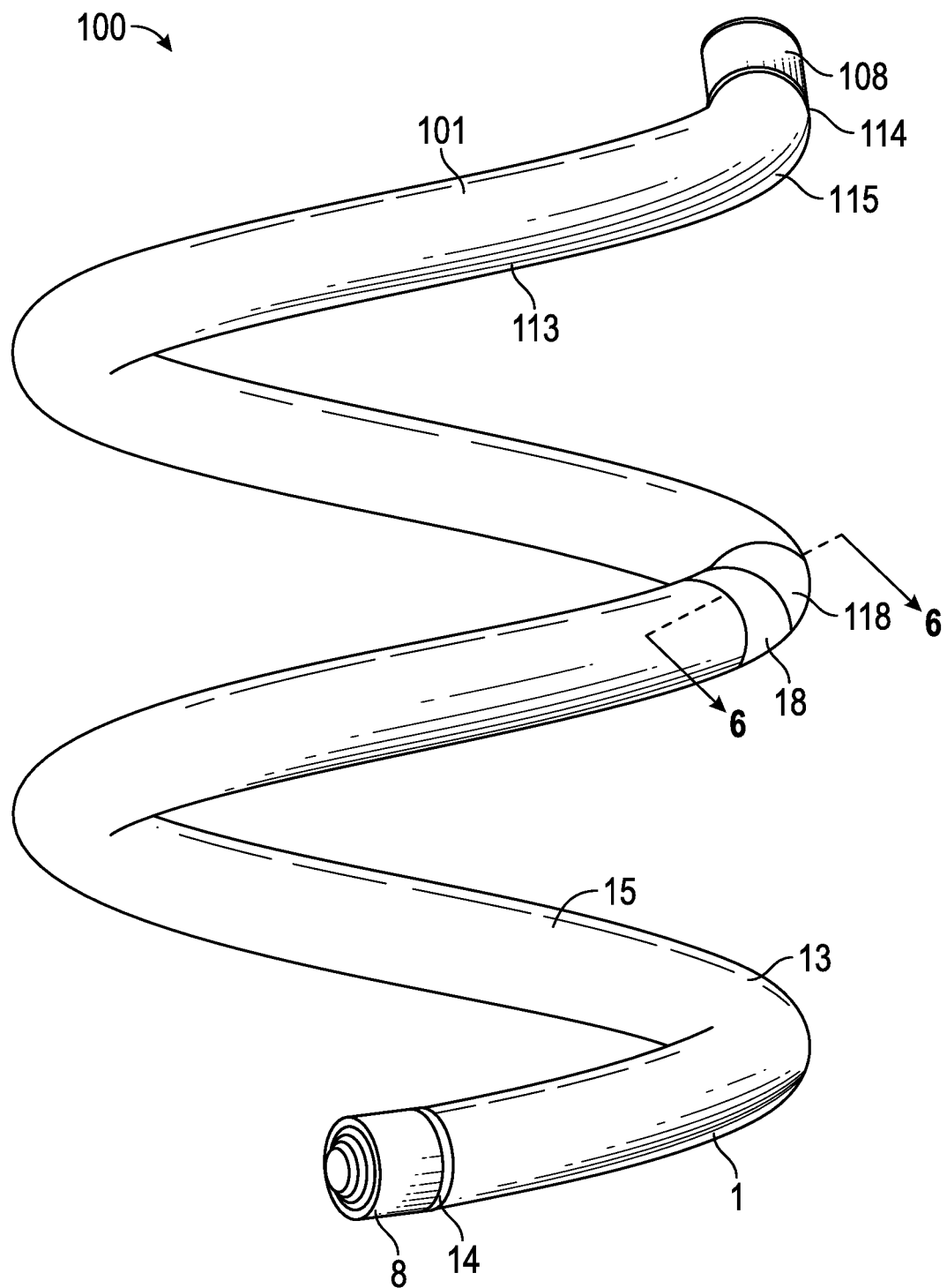
FIG. 5 is a perspective view of two sensor mounting systems of FIG. 1 joined at the ends according to an embodiment of the present disclosure.
Figure 6:
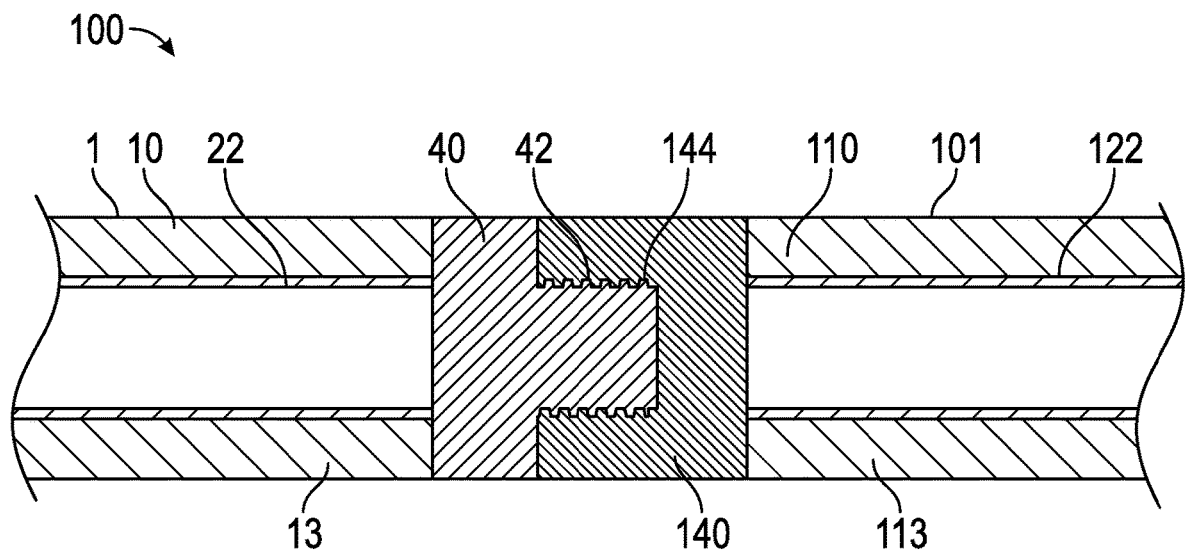
FIG. 6 is a cross sectional view of the sensor systems of FIG. 5 taken along line 5-5.

Referring now to FIGS. 5-6, an alternate sensor-mounting system 100 is illustrated. The sensor-mounting system 100 includes a first sensor-mounting system 1 and a second sensor-mounting assembly 101. The sensor-mounting assembly 101 is substantially similar to the sensor-mounting system 1, with the exception that the second end 120 of the body 110 has an opposed second coupling means 140, which may include a threaded aperture 144, such that the second coupling means 140 and 40 mate with each other. The coupling means 40 and 140 are illustrated as male and female threaded components 42 and 144, respectively, but may also be such coupling means as magnetic, compression, soldering, pressure fit, crimp fitting, or other methods known in the art or yet to be known (FIG. 6). It shall thus be understood by those of skill in the art that the sensor mounting systems 1, 101, etc. may be lengthened to accommodate additional components therein (e.g., batteries, computer components, etc.).

Referring back to FIG. 2, a sensor 9 for mounting into the sensor-mounting device 1 includes a microcontroller 44, a transceiver 46, memory 48, a power source 50, and one or more sensor nodes 52. Different sensors 9 and/or 9' (hereinafter collectively referred to as sensor 9) may be included as a part of the sensor-mounting system 1 in order to provide the ability to sense various desirable inputs and provide respective controlled responses as discussed below.

The sensor 9 is illustrated within a circular housing 53, though such housing and/or housing configuration is not required. At least part of the sensor housing 53 and related components may be situated within the central bore 24 of the inner tube 22. The sensor 9 may be any type of sensor, such as a motion (e.g., passive infrared), temperature, humidity, gas (e.g., radon, carbon monoxide), barometric pressure, smoke, optical or camera, light, sound (e.g., microphone) sensor, or a combination thereof. The sensors 9 may additionally be devices capable of transmitting information— e.g., speakers, lights, beacons, etc. In embodiments, sections of the body 10 may covered in a lightweight speaker cloth, for example.

The microcontroller 44 performs the tasks of processing the data received and controlled over the different components described below. The transceiver 46 may include a transmitter (or "antenna") 54. The antenna 54 may be situated outside the body 10, as the body 10 may act as a shield to RF communications. For example, the antenna 54 may be a part of circuitry located in the sensor head 8. The transceiver 46 may communicate directly and/or over a wireless communication infrastructure with other devices configured to receive such wireless communication to provide controlled response(s) to inputs from the sensor 9. The system 1 may be particularly configured for use on a 5G network, which may be useful for efficiently and quickly connecting together many devices and/or systems, as described herein, for the purpose of contributing to the Internet of Things.

In direct wireless communications, the transceiver 46 may include baseband processing circuitry to convert data into a wireless signal (e.g., radio frequency (RF), infrared (IR), ultrasound, near field communication (NFC), et cetera) and the transmitter 46 transmits the wireless signal. When a second wireless transceiver (not shown) is within range (i.e., is close enough to the first wireless transceiver 46 to receive the wireless signal at a sufficient power level), it receives the wireless signal and converts the signal into meaningful information (e.g., voice, data, video, audio, text, instructions for completing a task, et cetera) via baseband processing circuitry (e.g., through an application on a phone, computer, notepad, etc. or through a central display located within the home). Examples of direct wireless communication (or point-to-point communication) include Bluetooth, ZigBee, Radio Frequency Identification (RFID), et cetera.

For indirect wireless communication or communication via a wireless communication infrastructure, the first wireless transceiver 46 transmits a wireless signal to a base station or access point, which conveys the signal to a wide area network (WAN) and/or to a local area network (LAN). The signal may traverse the WAN and/or LAN to a second base station or access point to send signal to the second wireless transceiver or it may traverse the WAN and/or LAN directly to the second wireless transceiver. Examples of wireless communication via an infrastructure include cellular satellite/tower, IEEE 802.11, public safety systems, et cetera. The second wireless transceiver may wirelessly communicate back to the first wireless transceiver 46 in a similar manner.

The memory 48 contains the relevant computer or program instructions for the microcontroller 44, and may further store data obtained by the sensor node 52. The data may be transmitted by the transceiver 46 as described above. The memory 48 may be situated in the same circuit board as the microcontroller 44 and power source 50.

The sensor node 52 may be small in size and is the component that is measuring the particular activity being monitored (e.g., smoke, temperature, et cetera). The sensor node 50 is located in the sensor head 8 poking through an aperture 55 (FIG. 6). The sensor node 52 may optionally be a part of circuitry (e.g., the transceiver 46) housed in the sensor head 8. As noted above, each sensor 9 may include one or more sensor nodes 52. Each sensor node 52 may be configured to sense at least a single input and/or act as an output (e.g., LED, speaker, etc.). For example, a first sensor node 52 within a sensor 9 may be configured to measure the temperature in the room; a second sensor node 52 may be a light sensor for determining when the sun is out; a third sensor node 52 may be a camera. Additional sensor nodes 52 may further, or alternately, be incorporated into the sensor 9 as is desirable.

Those of skill in the art will appreciate that the sensor 9 may be any sensors that is currently on the market or may be later-developed. It shall further be appreciated that the sensor 9 (e.g., via sensor nodes 52) may be configured as an input and/or output device(s) (e.g., actuator, speaker, light/LED/laser, etc.) configured for Supervisory Control and Data Acquisition (SCADA) applications such as the Internet of Things (IoT). The sensors 9 may receive and provide information as part of a comprehensive distributed system throughout a location (or multiple locations, as the case may be). Sensors 9 may further sense harmful wave frequencies and provide controlled responses in the form of clean, healthy waves to counteract the harmful waveforms.

One or more sensors 9 (e.g., via sensor nodes 52) may be configured as a user interface as part of a distributed system. For example, the sensor(s) 9 may be in communication with various "smart systems" in a location in order to receive input (e.g., from the user) in order to effectuate a controlled response. The transceiver 46 may communicate with controlled response systems which may be situated within a home, such as a window that automatically shades at a certain temperature, or blinds that automatically open or close at a certain time or temperature, or as a response to another trigger from the sensor 9. In another example, the sensor 9 may be connected to the HVAC system of the home and able to control the HVAC system based upon the temperature measurements of the sensor node 52. Or, as noted herein, the sensors 9 may be equipped with nodes 52 which may include, among other things, microphones, cameras, lights, etc. In one example, the sensor 9 may have a microphone and may be configured (e.g., through programming) to recognize certain commands from a user. When a user says "set the thermostat to 72°'" the sensor 9 may communicate that message to the thermostat and set the temperature accordingly. Additionally, or alternately, the sensor 9 may communicate with the home alarm system if, for example, motion or another trigger is detected. Or, a sensor 9 may detect the presence of a person in a room which causes the lights to turn on. The sensors 9 may cause the lights in each room to turn on and/or off as the case may be as the user 2 walks from room to room with the system 1 attached thereto. Each sensor 9 distributed throughout a location may be equipped with such abilities, or the sensors 9 may be strategically removeably placed based on their specific abilities, i.e. camera or image recording. Those of skill in the art shall understand that the sensor 9 may be actively transmitting the signal (e.g., in real time or at predetermined intervals) or passively awaiting instructions to transmit.

Regardless of the capabilities of the sensor 9 (e.g., the number of sensor nodes 52), the sensor 9 may be exchangeable in order to provide greater (or less) functionality in the location and position where the sensor 9 is placed. The second sensor 9' may fit into the sensor-mounting device 1 in the same manner as the first sensor 9. Accordingly, it is understood that further components that make up the sensor 9 may be added to provide additional sensing features (e.g., temperature, motion, smoke, camera, et cetera).

The signals from various media (e.g., light, electrical waveforms, gases, fluids, radiation, etc.) may be distributed through the housing 54 (e.g., through the tube, a conduct, a light pipe, etc.) to the various systems (e.g., hardware) stored therein using time domain and/or frequency domain multiplexing. Examples of simple, low-cost network distribution methods include but are not limited to: serial data, CAN bus, LIN bus, Modbus, Inter-Integrated Circuit (I2C), and infrared data association protocol suite. In other words, a single signal may be transmitted using a simple wire, tube, or light pipe to power and bi-directionally communicate with the subsystems in the housing 54.

Wires and other component pieces associated with the various sensors 9 (e.g., wired connections to a power supply, batteries for power storage, etc.) may be housed within a central bore 24 of the inner tube 22. Therefore, unsightly cords, wires, etc. may be out of view, leaving only the sensor head 8 in view. When the sensor 9 is installed, the wires and/or component pieces may be fed through the central bore 38 of the coupling 14 and into the central bore 24 of the body 10 (FIG. 4). Wires are inherently flexible and the sensor 9 may flex with the manipulation of the body 10 as described herein. If a first sensor 9 is removed from the sensor-mount 1 (e.g., to replace it with another sensor), the wires and/or component pieces may be pulled back through the respective central bores 24 and 38, and the sensor 9 unhooked from the component pieces. The second sensor 9' may then be hooked to the component pieces, the wires and/or component pieces fed back through the respective central bores 38 and 24, and the sensor 9' secured into position with the sensor-mount 1 as described herein.

In one embodiment, certain electronics may be incorporated directly into the sensor head 8 thus allowing for increased versatility of the sensor 9. Here, the sensor head 8 may be equipped with electrical leads, such as metal pads. The electrical leads on the sensor head 8 may correspond to electrical leads on the coupling 14. The electrical leads on the coupling 14 may be wire connected to the battery 50 and other electrical components of the sensor 9 (e.g., microcontroller 44 and memory 48), which may be housed in the central bore 24 as discussed above. When the electrical leads on the sensor head 8 come into contact with the electrical leads on the coupling 14, the circuit may be completed. The sensor nodes 52 may be able to send information to the microcontroller 44 and memory 48, and the sensor 9 may receive power from the battery 50.

In this embodiment, the electrical components housed in the central bore 24 may be comprehensive. In other words, the circuitry required to utilize many different types of sensors 9 (and/or sensor nodes 52) may be readily available if the chosen sensor 9 has nodes 52 to take advantage of such functionality. Where the sensor 9 does not have a node 52 for certain functionality, that portion of the circuitry may simply stay dormant. For example, circuitry for a sensor 9 having nodes 52 to measure and/or detect light, temperature, humidity, and movement may be provided in the central bore 24. The circuitry may be connected, using methods known of skill in the art, to the electrical leads on the coupling 14. A sensor 9, however, may only have nodes 52 configured to measure light, heart rate, real time or still images, temperature, and humidity. Therefore, the circuitry related to the detection of movement may remain available yet inactive. If a sensor 9 is later provided that has a node 52 for detecting movement, the circuitry related to such detection of movement may be utilized.

It shall be recognized that electrical leads may additionally (or alternately) be located in the sensor mounting device 1. The electrical leads in each device may be configured to engage with electrical leads on the other respective device(s) in order to complete the circuit between the sensor nodes 52 and the required electrical circuitry stored in the central bore 24. The electrical leads may also be on the sensor 9 itself and/or on the sensor head 8, such that the circuit is completed when the sensor head 8 is secured to the body 10.

Figure 7:
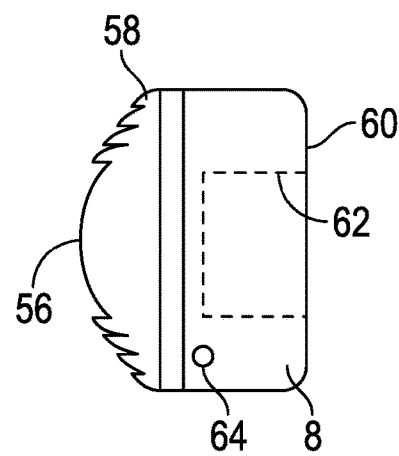
FIG. 7 is a side view of a sensor head in a first embodiment.
Figure 8:
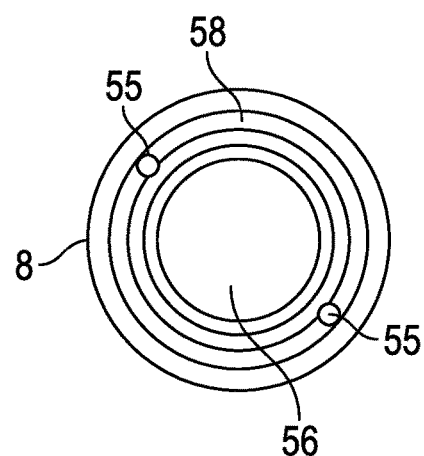
FIG. 8 is a front view of the sensor head of FIG. 7.

The sensor head 8 is the face or cover of a sensor-mounting system 1. The sensor head 8 connects or mates with the second end 36 of the coupling 14 to effectively seal the sensor 9 within the body 10. The sensor head 8 includes a first end 56 having a cap 58 and a second end 60 having a coupling means 62 (FIG. 7). The male threaded portion 34 (FIG. 2) at the first end 16 of the body 10 is secured to the coupling means 62 at the second end 60 of the sensor head 8. In another embodiment, the sensor head 8 may have a "snap on" configuration, wherein the sensor head 8 is equipped with means for snapping into position with the mounting device 1, such as a bayonet mount which is well known in the art. The sensor head 8 may have release buttons for releasing the sensor head 8 from the "snapped" position with the mounting device 1. In still a further embodiment, the sensor head 8 may be configured for a quarter-turn or half-turn snap fit with the mounting device 1. Such methods of mounting are known in the art. In yet another embodiment, the sensor head 8 may be threaded, the threads on the sensor head 8 corresponding to threads in the mounting device 1. The sensor head 8 may thus be simply screwed into position with the mounting device 1. In still a further embodiment, the sensor head 8 may be magnetically coupled to the mounting device 1. The sensor head 8 and mounting device 1 may be equipped with corresponding magnets (e.g., rare earth magnets) which may be positioned and polarized in patters that allow for perfect positioning of the sensor head 8 within the mounting device 1. The force exerted in pulling the sensor head 8 away from the mounting device 1 must overcome the magnetic forces to remove the sensor head 8 from the mounting device 1. The sensor head 8 may optionally or alternately include other coupling means, such as male/female, elastic fit, cam, or other fastening means, whether now known or later developed.

The sensor head 8, and especially the cap 58, may form an ornate component of the sensor-mounting system 1. The cap 58 may be any geometrical shape (e.g., square, rectangular, oval, irregular, 3-dimensional (e.g., conical) et cetera) or any other desirable configuration. The cap 58 may be transparent, opaque, cosmetically designed (e.g., in color and in shape), and/or virtually invisible such that it blends the body 10 and/or with its surroundings. In this way, the sensor 9 may be specifically designed to be seen or not seen, depending on the preferences of the user.

Further, the sensor head 8, optionally together with other portions of the system 1 (i.e. body 10) may act as a component of other aesthetic pieces such as artistic renderings, pictures, or non-static displays, such as OLED, LED, LCD, et cetera. The cap 58 may cover the first end 16 of the body 10 or may be as large to cover the front flange 30 of the coupling 14 or any size thereof. As noted herein, the sensor head 8 may have a Fresnel lens configuration. Also, as noted, the Fresnel lens may be utilized to capture more light or UV energy for charging a solar battery power source 50 and/or may be used for an infrared motion sensor.

The sensor head 8 may include at least one small pin hole 64 such that a small item (e.g., a paper clip) may be used to rotate the sensor head 8 into position. In some embodiments, the sensor head 8 may only require a quarter turn to be fully locked into place. Alternately, at least one of the first and second ends 56 and 60 may further include a nut configuration, so as to torque the sensor head 8 onto the coupling 14. Embodiments of the sensor head 8 may have a variety of configurations. Additional embodiments of a sensor head are illustrated in FIGS. 9-14.

Figure 9:
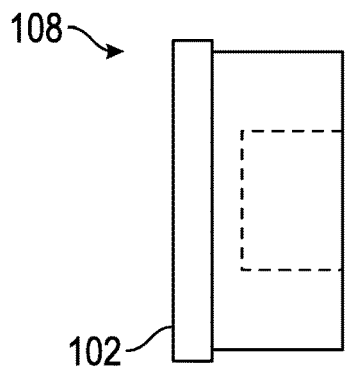
FIG. 9 is a side view of a sensor head in a second embodiment.
Figure 10:
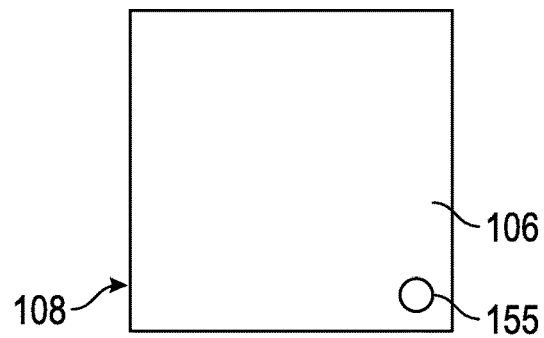
FIG. 10 is a front view of the sensor head of FIG. 9.
Figure 11:
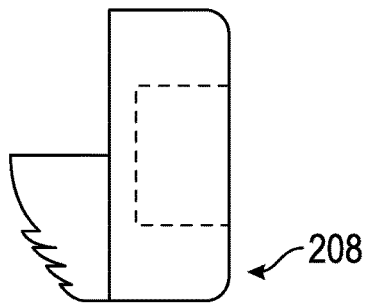
FIG. 11 is a side view of a sensor head in a third embodiment.
Figure 12:
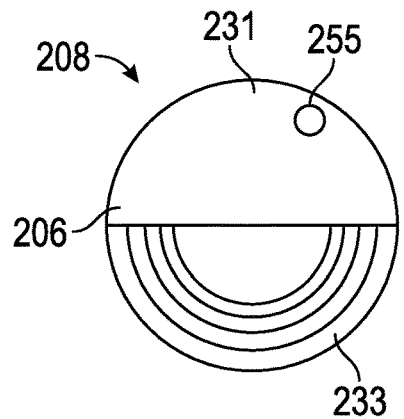
FIG. 12 is a front view of the sensor head of FIG. 11.
Figure 13:
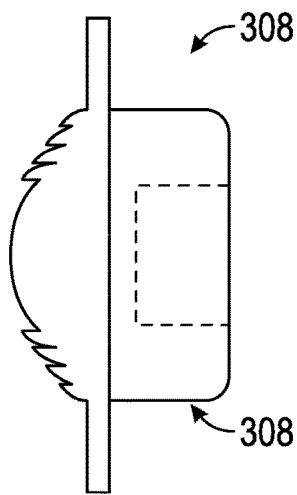
FIG. 13 is a side view of a sensor head in a fourth embodiment.
Figure 14:
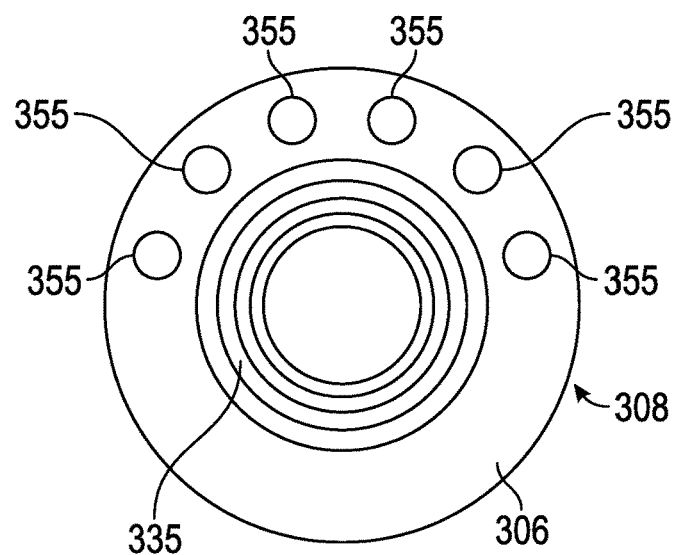
FIG. 14 is a front view of the sensor head of FIG. 13.

Referring to FIGS. 9-10, a sensor head 108 has a square face 106 with one or more sensor apertures 155 into which a sensor node 52 may be situated. Referring now to FIGS. 11-12, a sensor head 208 has a split face 206 with an upper portion 231 having one or more sensor apertures 255 and a bottom portion 233 being a Fresnel lens. Referring to FIGS. 13-14, a sensor head 308 has face 306 with a central Fresnel lens portion 335, with sensor apertures 355.

The sensor 9 may further include indicators that may also be situated within the sensor head, such as a light source (e.g., LED, laser, OLED, electroluminescent lamp (EL Lamp), etc.) or an audible alarm that is triggered once a particular activity is sensed (e.g., smoke, gas, motion). Such indicators may be part of circuitry housed in the sensor head 8 and/or the housing 54. Still further, the sensor 9 may be a light beam displacement device, such as a mirror galvanometer. As noted above, the mating of the sensor head 8 with the coupling 14 of the body 10 may complete a circuit and power specific electronics housed in the sensor head 8 (e.g., transceiver 46, sensor node 52, light source, et cetera).

In a further embodiment, the system 1 is configured as a personal health device. Here, the sensor head 8 may be configured as an internal screening apparatus. The sensor head 8, for example, may include a mouthpiece with one or more sensors 9 for evaluating the health of the user via the user's mouth. The sensors 9 may include a thermometer, a camera, sensors for measuring bacteria, etc. In embodiments, the sensor head 8 may be in remote communication (e.g., over a network) with a third party device, such as a phone or personal computer. Using methods that comply with HIPAA regulations, the health information from the mouthpiece may be transmitted over the network to the third party device such that the third party (e.g., a healthcare professional) can provide remote health care to the user. The health care provider may be able to communicate with the user (e.g., via speakers located somewhere along the body 10) to direct the user to move the sensor head 8 to a desired location. In this way, doctors may be able to treat patients remotely, and may be able to provide more timely care to their patients. Prescriptions may be remotely prescribed, or the patient may be directed to take a certain action until the user is able to be seen in person. It shall be understood that, in addition to a mouthpiece configuration, the sensor head 8 may additionally, or alternately, be configured for use anywhere in or near the body. For example, the sensor head 8 may take the form of an ear piece which may be used by a user during consultation with an ENT. In still another configuration, the sensor head 8 may be small enough to insert into the user's nostril(s) without significant discomfort such that a healthcare professional can see into the user's sinuses (or thereabouts). In still another embodiment, the sensor head 8 may have a small hole formed therein, such that fluids (e.g., blood) may be received into the sensor head 8 to contact a sensor 9, which may measure certain attributes of the fluid. Further configurations are contemplated within the scope of the invention as is understood by those of skill in the art.

An important aspect in the development of a wireless sensor 9 is ensuring that there is adequate energy available to power the system. The sensor 9 consumes power for sensing, communicating, and data processing. More energy is required for data communication than any other process. It may be beneficial for the system 1 to include means for storing power. The power source 50 may be capacitors or a battery, such as NiCd (nickel-cadmium), NiZn (nickel-zinc), NIMH (nickel-metal hydride), or lithium-ion. The battery 50 may be configured to receive electrical energy during hours of non-use (e.g., by plugging into an electrical energy source). Alternately, or additionally, the battery 50 may store energy from other sources which may then be converted into electrical energy for use by the sensor 9. For example, the sensor 9 may be able to capture solar energy through a photo-voltaic cell, which may be stored in the battery 50 according to methods known to those of skill in the art. The sensor material 13 may be flexible light pipe(s), which may be partially situated about the inner tube 22, with at least a portion (e.g., a lens) having exposure to ambient or artificial light. Light pipes are well known in the industry, and are specifically known for transporting and/or distributing light. Any light pipe currently available or hereinafter made available may be utilized within the scope of the invention. Further, it shall be understood that the housing 54 may itself be a light pipe.

The light pipe(s) may include a dome for collecting and reflecting as much light as possible into the tube. To optimize solar light, a heliostat may be installed so as to direct sunlight into the tube at all time. Further, the heliostat may allow the light pipe to capture light from the moon at night. Typically, light pipes direct light to another location which may have little to no access to natural light. Here, however, the light may be transferred through the light pipe to a photo-voltaic cell. Those of skill in the art shall recognize that reflective coatings on an inside surface of the light pipe(s) may be beneficial for maximizing the energy harvesting potential.

Figure 15:
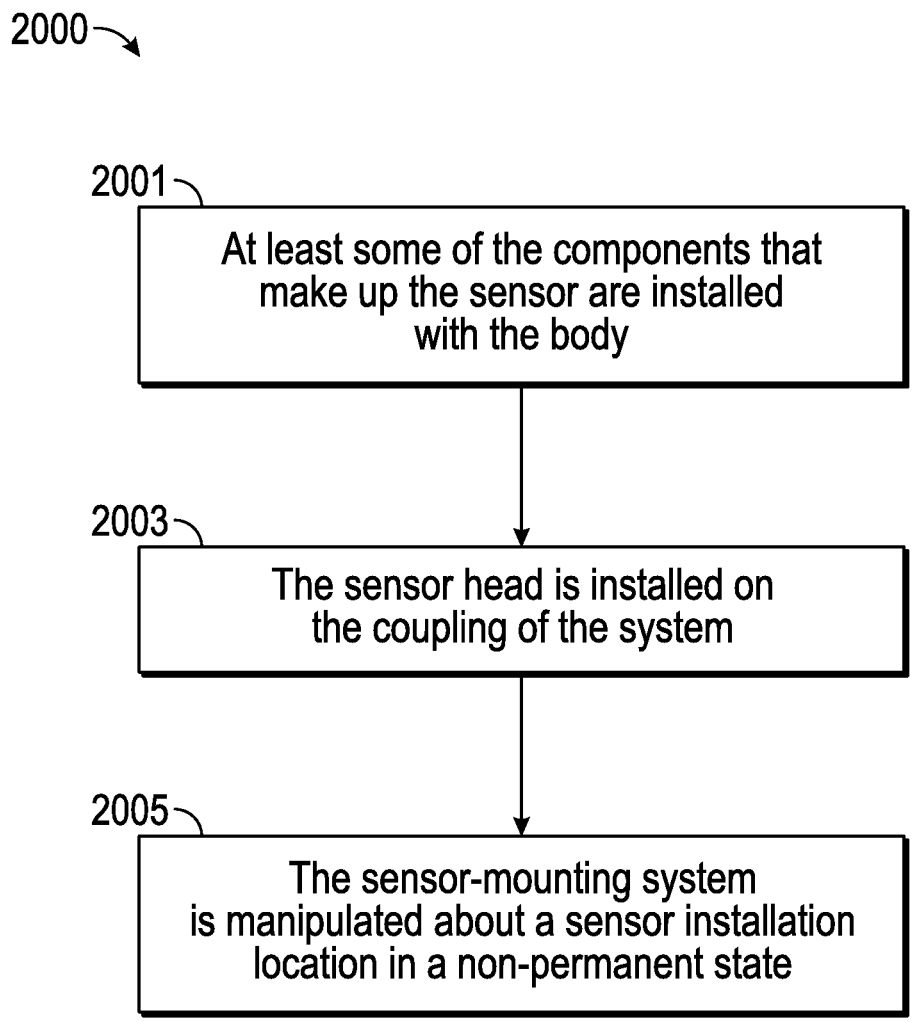
FIG. 15 is a flow diagram of a method of installing the sensor-mounting system of FIG. 1 according to an embodiment of the present disclosure.

Referring to FIG. 15, a method 2000 of installing a sensor-mounting system 1 is illustrated. In this method, only the method as it pertains to the sensor-mounting device 1 is disclosed, but the steps for the other embodiments of the sensor-mounting systems 100 would be similar.

In step 2001, at least some of the components that make up the sensor 9 are installed within the body 10. The components pass through the central bore 38 of the coupling 14 and into the central bore 24 of the inner tube; therefore the electronics are sized and shaped to be elongate and small enough to fit through these bores. If at least some of the components of the sensor 9 are housed in the sensor head 8, then wiring or other electrical connecting means may be exposed until after the sensor head 8 is installed. The sensor may be off initially and turned to an on position once installed.

In step 2003, the sensor head 8 is installed on the coupling 14 of the system 1. In some embodiments, the sensor head 8 may require a quarter-turn rotation to install. Electronic connecting means may fully connect and complete the circuit to communicate with at least some of the components of the sensor 9, such as the microcontroller 44, memory 48, a power source 50, et cetera.

In step 2005, the sensor-mounting system 1 is manipulated about a sensor installation location in a non-permanent state. In this step, the flexible, poseable, material 13 may be spun, tied, crossed over, or otherwise manipulated and held in a non-permanent state (e.g., FIG. 3) until manipulated to another position or state. Various steps of the method 2000 may be performed out of the sequenced disclosed above.

Additionally, various embodiments of sensor mounting systems identical or similar to those described herein may be adapted for other uses in addition to those described herein. Here, those of skill in the art will appreciate that various components may be designed to be waterproof and/or to dissipate heat, among other features, in order to handle the potentially harsh environment in which the sensor may be placed. In another example, one or more sensing mounting systems may be configured for permanent placement in concrete (e.g., sidewalk, roadways, etc.), but with a flexible body to manipulate location of sensor 9. The sensor mounting system may be configured to withstand compression and expansion of a concrete environment. The sensor mounting system incorporated into a concrete may be particularly useful, in some embodiments, as a self-charging (e.g., using solar power) light, similar to those available on the market today. Here, the sensor may incorporate means for receiving and storing solar energy, as described above, as well as various lighting capabilities for transmitting light (e.g., when the sensor determines that such light is desirable. Further implementations of the various sensor mounting devices shall be understood to be within the scope of the invention.

Many different arrangements of the various components depicted, as well as components not shown, are possible without departing from the spirit and scope of the present invention. Embodiments of the present invention have been described with the intent to be illustrative rather than restrictive. Alternate embodiments will become apparent to those skilled in the art that do not depart from its scope. A skilled artisan may develop alternate means of implementing the aforementioned improvements without departing from the scope of the present invention. Further, it will be understood that certain features and subcombinations may be of utility and may be employed without reference to other features and subcombinations and are contemplated within the scope of the claims.

The invention claimed is:

1. A sensor-mounting device comprising:
   an elongated tubular body having a front end, a rear end, and a bore extending between the front and rear ends in a longitudinal direction;
   a first coupling portion on the front end and a second coupling portion on the rear end; and
   a first sensor located within the bore of the tubular body;
   wherein:
      the first coupling portion comprises:
         a first plate having a central bore formed therein and a threaded projection extending therefrom for at least partially receiving the first sensor; and
         a first end cap, wherein a bottom surface of the first end cap abuts a top surface of the first plate in an installed configuration;
      the second coupling portion comprises a second plate having a threaded projection extending therefrom, and a second end cap having a threaded bore formed therein, wherein the threaded bore of the second end cap mates with the threaded projection of the second plate;
      the first coupling portion and the second coupling portion are separable from the elongated tubular body; and
      the tubular body is flexibly poseable and fixable into a non-permanent position.

2. The sensor-mounting device of claim 1, further comprising an inner tube having a central bore, the inner tube being located within the bore of the tubular body, and the first sensor being located within the inner tube central bore, and wherein the inner tube is poseable and fixable into the non-permanent position.

3. The sensor-mounting device of claim 1, wherein the tubular body is generally circular in cross section.

4. The sensor-mounting device of claim 1, wherein the first sensor includes at least one sensor node and a transceiver, the transceiver configured to transmit data collected from the sensor node over a network.

5. The sensor-mounting device of claim 4, wherein the first end cap is configured as a decorative end.

6. The sensor-mounting device of claim 5, wherein at least one of the sensor node and the transceiver are located in a sensor head recess.

7. The sensor-mounting device of claim 5, wherein, when the first end cap is attached to the body, a sensor circuit is connected.

8. The sensor-mounting device of claim 1, wherein the second end cap covers the second plate.

9. The sensor-mounting device of claim 1, wherein the second end cap includes a tip configured to be driven into a surface.

10. The sensor-mounting device of claim 4, wherein the first sensor is at least one of a motion detector, a temperature detector, a humidity detector, a gas detector, a pressure detector, a liquid detector, smoke detector, a camera, a light detector, and a sound detector.

11. The sensor-mounting device of claim 1, wherein the body is made from foam.

12. The sensor-mounting device of claim 10, wherein the sensor-mounting device modularly includes a second sensor selected from the list consisting of: a motion detector, a temperature detector, a humidity detector, a gas detector, a pressure detector, a liquid detector, smoke detector, a camera, a light detector, and a sound detector; wherein the second sensor includes at least one sensor node different from the at least one sensor node of the first sensor, and wherein the first end cap comprises an aperture for receiving the respective sensor nodes of the first and second sensors.

13. The sensor-mounting device of claim 4, wherein the sensor-mounting device is an internal screening apparatus, and wherein a user uses the internal screening apparatus to determine at least one health attribute of the user.

14. The sensor-mounting device of claim 13, wherein the at least one health attribute is transmitted over the network to a third party.

15. The sensor-mounting device of claim 13, wherein the internal screening apparatus is configured as one of: a mouthpiece, a bacteria sensor, an earpiece, and a biosensor for determining an attribute of a fluid.

16. The sensor-mounting device of claim 1, wherein the tubular body is a flexible light pipe.

17. The sensor-mounting device of claim 16, wherein the first end-cap comprises a dome for collecting light.

18. The sensor-mounting device of claim 17, further comprising a photo-voltaic cell, wherein the light from the dome is transferred through the light pipe to the photo-voltaic cell, wherein the light is converted to storable energy for later use.

19. The sensor-mounting device of claim 1, wherein a radius of the first plate is larger than a radius of the tubular body.

* * * * *